United States Patent [19]

Plambeck, Jr.

[11] 4,211,561

[45] Jul. 8, 1980

[54] METHOD OF PRODUCING CROSS-LINKED POLYMERIC IMAGES

[75] Inventor: Louis Plambeck, Jr., Wilmington, Del.

[73] Assignee: E. I. Du Pont de Nemours and Company, Wilmington, Del.

[21] Appl. No.: 968,031

[22] Filed: Dec. 8, 1978

[51] Int. Cl.$^2$ .......................... G03C 5/00; G03C 7/00
[52] U.S. Cl. .................................. 430/306; 430/275; 430/380; 430/382; 430/435; 430/566; 430/627
[58] Field of Search ............... 96/100 R, 115 P, 86 P, 96/66 R, 55, 35.1, 95

[56] References Cited

U.S. PATENT DOCUMENTS

| | | | |
|---|---|---|---|
| 3,070,442 | 12/1962 | Cohen et al. | 96/115 P |
| 3,406,067 | 10/1968 | Cerwonka | 96/115 P |
| 3,856,524 | 12/1974 | Bissonette | 96/35 |
| 4,003,747 | 1/1977 | Tsunoda et al. | 96/86 P |
| 4,137,080 | 1/1979 | Fujiwhara et al. | 96/100 R |

*Primary Examiner*—J. Travis Brown

[57] ABSTRACT

The invention is directed to a process for producing cross-linked polymeric images on a substrate employing an oxygen-insensitive silver halide system to obtain camera-speed imaging with good resolution of the resulting image. The process comprises imagewise exposing a photosensitive layer containing dispersed silver halide in operative association with a multifunctional hydrophilic polymeric coupler, developing the exposed layer with a multifunctional developing agent, and removing the undeveloped, noncross-linked areas by washing with a solvent.

19 Claims, No Drawings

METHOD OF PRODUCING CROSS-LINKED POLYMERIC IMAGES

DESCRIPTION

1. Technical Field

This invention relates to an image-forming process involving a photosensitive layer comprising silver halide and a polymeric polyfunctional coupler which is cross-linked by developing with a polyfunctional developing agent. The invention also relates to the removal of uncross-linked coupler by washing.

2. Background Art

The use of dye-forming polymeric polyfunctional couplers in color photography has been previously described. U.S. Pat. No. 2,310,943 to Dorough et al. describes the use of a polyvinyl acetal carrying phenolic color former groups, e.g. polyvinyl salicylal prepared by the reaction of polyvinyl alcohol and salicylaldehyde, dispersed in a gelatin/silver halide photographic emulsion. Exposure to light followed by development with a color-forming developer, e.g. p-aminodiethylaniline, gave a colored image. Dorough also discloses that the polyvinyl acetal coupler can react with an aromatic diazo compound to form a polymeric azo dye. U.S. Pat. Nos. 2,397,864 and 2,397,865 to Jennings et al. disclose the use of the acetals disclosed by Dorough et al. and related hydrophilic polymeric color formers as the sole film-forming carrier for silver halide in a color film. In such use the polymeric color former is insoluble in water at 30° C., and development is carried out with a conventional color-forming developer. Washout of unexposed undeveloped areas is not disclosed.

Procedures whereby imagewise exposing gelatin/silver halide layers are developed under conditions that cause tanning of the gelatin in the exposed areas are well-known and have been widely used to prepare gelatin relief images useful in the imbibition printing of color pictures, e.g. Tull, J. Photog. Sci., 24, 158–167 (1976). Although monofunctional developers are generally used as gelatin tanning agents in such a procedure, U.S. Pat. No. 3,440,049 to Moede describes the use of bifunctional developers, namely polyhydroxyspiro-bisindanes. The gelatin relief images obtained are not sufficiently abrasion-resistant for many applications.

In U.S. Pat. No. 2,661,291, Slifkin describes the use of tetrazo derivatives of selected diamines of the formula

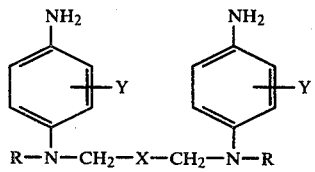

wherein X is a radical of the class consisting of —(CH$_2$)$_n$—, —(CH$_2$)$_{n'}$—O—(CH$_2$)$_{n'}$—, —(CH$_2$)$_{n'}$—CHOH—(CH$_2$)$_{n'}$—and

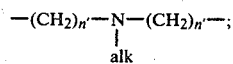

R is H, alkyl or hydroxyalkyl; n is 0–8; n' is 0–4; and Y is H or alkyl, in light sensitive, nonsilver coatings containing a diazotype coupling component, and in U.S. Pat. No. 3,778,270 Roos combines such light sensitive bis-diazonium salts with a macromolecular organic polymer having pendant reactive groups so that after imagewise exposure to light and treatment with an alkali, the polymer in the unexposed areas is cross-linked and insolubilized by azo coupling. Although a wide variety of polymers can be cross-linked by this procedure, the light sensitivity of the bis-diazonium salt is very low compared to a silver halide system.

In U.S. Pat. No. 3,694,138 Kalopissis et al. disclose N,N'-diaryl alkylenediamines of the type used in the Slifkin patent in combination with an oxidizing agent as useful for dyeing hair. Such diamines may be used in the presence or absence of added couplers. U.S. Pat. No. 3,904,418 discloses the use of a polymerized monomer containing at least one active methylene group as a component of a binding agent, useful in a photographic element adapted for silver-dye bleach processes. Conventional photographic developers are employed.

German Patent Specification No. 2,650,764 broadly discloses a process for preparing color pictures by means of light-sensitive, photographic, silver halide reproducing materials in which development occurs with a polyfunctional developing agent, including alkylenediamines of the type disclosed by Slifkin, in the presence of a polyfunctional coupler, e.g. an aminophenol. The use of polymeric polyfunctional couplers is disclosed but none are exemplified. Washout of unexposed undeveloped areas is not disclosed.

DISCLOSURE OF INVENTION

According to the present invention, there is provided a method for producing a cross-linked polymeric image on a substrate which comprises:

(a) imagewise exposing a photosensitive element to actinic radiation, said element comprising a substrate coated with a photosensitive layer containing dispersed silver halide in operative association with a continuous film-forming phase of hydrophilic polymeric coupler having a number average molecular weight of about 5,000 to about 100,000 and containing, per polymer chain, an average of at least two coupler groups capable of coupling with an oxidized p-aminodialkylaniline;

(b) swelling the polymeric coupler, and developing the exposed layer with a developing agent containing at least two functional groups capable of selectively reducing a silver halide latent image and, in their oxidized state, capable of coupling with the coupler groups of the swollen polymeric coupler, whereby the polymeric coupler is insolubilized by cross-linking, thereby forming an image; and (c) removing the undeveloped, noncross-linked areas of the polymeric coupler by washing with a solvent in which the noncross-linked areas are soluble.

BEST MODE

The instant invention provides a novel process for preparation of a cross-linked polymeric image on a substrate employing silver halide to obtain imaging with a wide range of speeds including camera speed with good resolution of the resulting image. In addition the process is operable with silver halide coating weights as low as about 2 mg/dm$^2$. The process is applicable for a wide variety of pattern and image yielding uses including the preparation of lithographic films and plates, and computer output microfilm. An advantage of the system used in the process of the invention is that it is oxygen-insensitive compared with conventional photopolymerizable imaging systems.

The process of the invention may be employed for the preparation of both negative and positive images. In the preparation of a negative image, the areas insolubilized by cross-linking correspond to the areas exposed to light, whereas for a positive image, the areas insolubilized by cross-linking correspond to the unexposed areas. The type of image obtained depends on the character of the silver halide used. Thus, a normal negative-working silver halide yields a negative cross-linked polymer image while a positive-working silver halide (e.g. prepared by such well-known techniques as solarization or chemical fogging) yields a positive polymer image.

The process of the invention employs a photosensitive element, said element comprising a substrate coated with a photosensitive layer containing dispersed silver halide in operative association with a film-forming hydrophilic polymeric coupler which contains a plurality of coupler groups. Although the work of Jennings et al. described in U.S. Pat. No. 2,397,864 utilizes a hydrophilic film-forming polymeric coupler, e.g. polyvinyl salicylal, as the silver halide carrier, most polymeric couplers in the prior art have been used in admixture with gelatin which serves as the film former and silver halide carrier. Thus, ordinarily the polymeric coupler merely provides a non-diffusing dye image after coupling with the oxidized developing agent. For a discussion of polymeric couplers see "The Theory of the Photographic Process", Fourth Edition, edited by T. H. James, Macmillan Publishing Co., Inc., New York, 1977, pages 347–348.

In the instant invention the polymeric coupler must be present as a continuous phase in operative association with the silver halide. The silver halide may be dispersed in the polymeric coupler phase itself, or it may be contained in a layer of a binder adjacent to the polymer coupler phase. Such a binder layer is preferably a gelatin layer overlying the polymeric coupler phase. Minor amounts of gelatin may be present in the polymeric coupler phase so long as the coupler provides the continuous phase.

The hydrophilic polymeric coupler of the invention has a number average molecular weight of about 5000 to about 100,000 and contains an average of at least two equivalents of coupler groups per polymer chain to provide for effective cross-linking. The molecular weight of the polymeric coupler is determined in any specific case by balancing ease of washing out the uncross-linked areas with good mechanical properties. For example, low molecular weight polyvinyl salicylal couplers are more easily removed in the uncross-linked areas after development, but the films tend to be somewhat weak. Alternatively, high molecular weight polyvinyl salicylal couplers give films of good mechanical properties, but the uncross-linked areas are difficult to remove by washout. Preferred polymeric couplers have a number average molecular weight of about 10,000 to about 50,000 and contain about 0.1 to about 1.0 equivalent of coupler group per 1000 g of polymer.

The coupler groups may be any of the conventional coupler groups employed in color photography which are capable of coupling with an oxidized p-aminodialkylaniline to form a dye. Such coupler groups include, but are not limited to phenols, naphthols, amines, aminophenols, bis-phenols, pyrazolones, acylacetarylides, cyanoacetarylides, betaketoesters, N-homophthalylamines, coumaranones, indoxyls, thioindoxyls, and the like, and as further disclosed in U.S. Pat. No. 2,397,864.

The coupler groups may be attached to any suitable hydrophilic base polymer so as to obtain the hydrophilic polymeric coupler of the invention as defined above. Preferred base polymers include polyvinyl alcohol; partially hydrolyzed polyvinyl acetate; hydrolyzed copolymers of vinyl acetate and other conventional vinyl monomers; homopolymers of acrylic acid, methacrylic acid, methacrylamide, and 2-hydroxyethyl methacrylate; copolymers of acrylic acid, methacrylic acid, methacrylamide, and 2-hydroxyethyl methacrylate with other conventional vinyl monomers; poly(ethylene oxide); polyvinyl pyrrolidone; copolymers of maleic anhydride, etc.

The coupler groups are usually attached as lateral substituents on the main chain of the hydrophilic base polymer, and they can be incorporated using such conventional chemical processes as esterification, amidation, etherification, acetal formation, etc. For example, reaction of polyvinyl alcohol with salicylaldehyde in the presence of an acid catalyst gives polyvinyl salicylal. Similar reaction of polyvinyl alcohol with other amino and hydroxy-substituted aromatic aldehydes gives polyvinyl acetals with attached coupler groups.

Preparation of hydrophilic polymers which contain coupler groups can also be accomplished by copolymerization of an ethylenically unsaturated monomer which contains a coupler group, e.g. 1-phenyl-3-methacrylamido-5-pyrazolone, with such other monomers as methyl methacrylate, ethyl methacrylate, ethyl acrylate, propyl acrylate, etc., together with such monomers as methacrylic acid, acrylic acid, methacrylamide, 2-hydroxyethyl methacrylate, and the like, to provide hydrophilic polymers which contain pyrazolone groups attached to the polymer chain. Other useful ethylenically unsaturated monomers which contain color-forming coupler groups are disclosed in British Pat. No. 875,248. Additionally, the pyrazolone coupler group can be attached to a polymer chain by reaction of 1-p-aminophenyl-3-methyl-5-pyrazolone with anhydride groups in a polymer chain, e.g. with a styrene/maleic anhydride copolymer.

Likewise, preparation of polymers which contain ketomethylene coupler groups can be carried out by polymer substitution reactions. For example, reaction of ethyl acetoacetate with polyvinyl alcohol in an ester exchange reaction gives a hydrophilic polymer which contains a plurality of ketomethylene groups.

The polymeric couplers are cross-linked, after exposure, by treatment with a developing agent containing at least two functional groups capable of selectively reducing silver halide latent image and, in their oxidized state, capable of coupling with the coupler groups of the polymeric coupler. Since at least two such reducing groups are present in the developing agent and since the coupler groups are attached to polymer chains, cross-linking of the polymer chains takes place as a result of the coupling reaction. Such cross-linking is shown in Equation (1) for salicylal coupler groups and a bifunctional diamine developing agent.

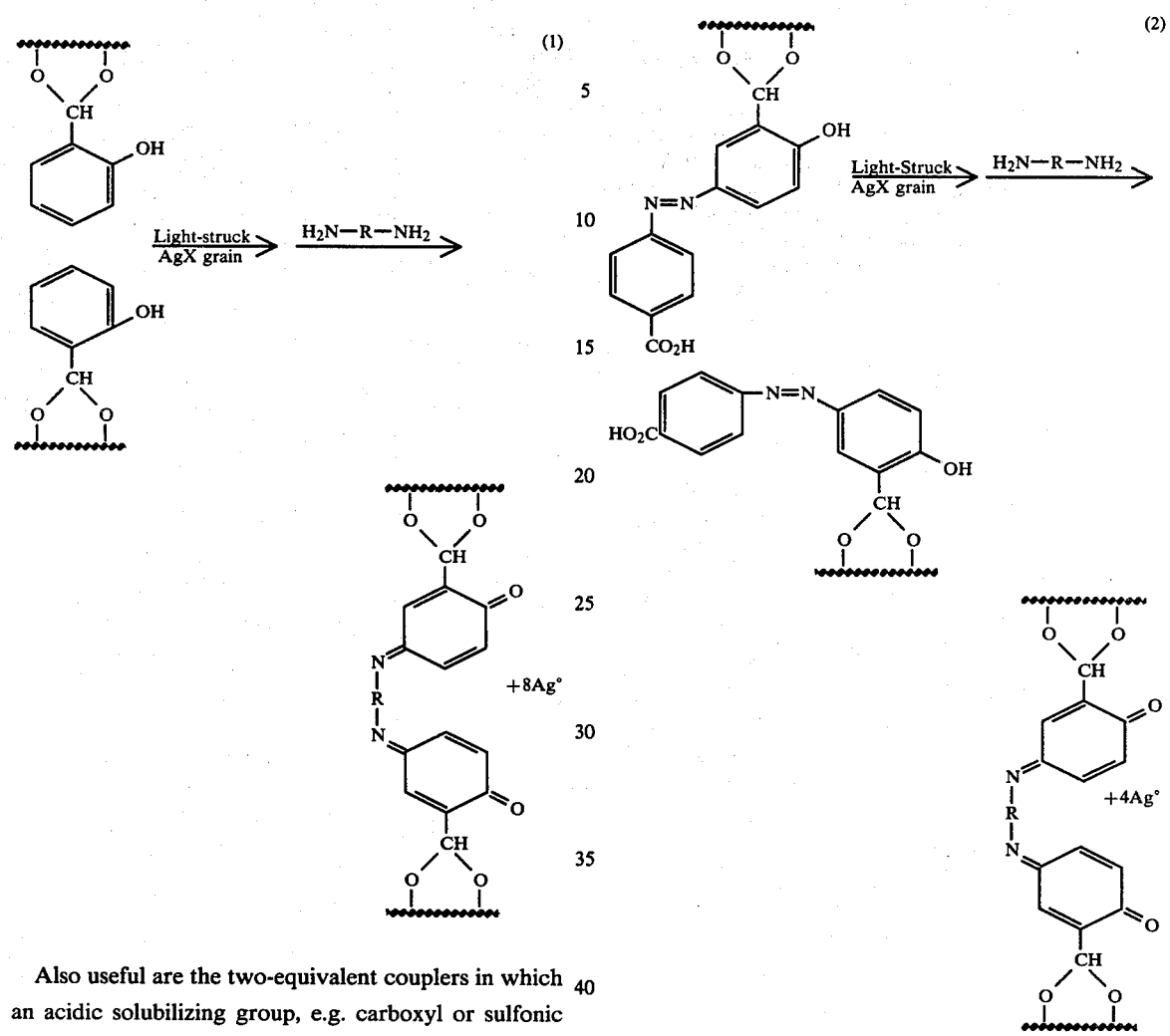

Also useful are the two-equivalent couplers in which an acidic solubilizing group, e.g. carboxyl or sulfonic acid, is present in a coupling position so that when an oxidized developing agent couples to form a cross-linked polymer the acidic group is lost. This combination of events leads to a marked change in solubility of the developed areas wherein a solubilizing group is lost and an insolubilizing cross-link is developed as compared with the undeveloped areas. For a discussion of two-equivalent couplers, see pages 341-342 of "The Theory of the Photographic Process", vide supra.

It is also possible to have the solubilizing group in a two-equivalent coupler attached to another portion of a molecule that is removed during the coupling reaction. For example, couplers are known which contain a removable azo linkage, ArN=N—, in the coupling position. Thus, reaction of diazotized p-aminobenzoic acid with polyvinyl salicylal gives a polymeric coupler which contains the removable azo linkage in the coupling position (Ar=p-carboxyphenyl) in accordance with the equation:

The carboxyl group is removed along with the azo group during coupling.

Preferred hydrophilic polymeric couplers include polyvinyl salicylal and hydrophilic polymers which contain pyrazolone coupler groups.

When indoxyl groups are employed as coupler groups, the process of the invention may be carried out without employing a separate developing agent. Indoxyl groups in alkaline solution can function as developing agents in that such groups are capable of selectively reducing a silver halide latent image and in their oxidized state they can react with a second molecule of oxidized indoxyl to form an indigo-type of cross-linked image.

In addition to the usual sensitizers and sensitizing dyes used for conventional silver halide emulsions, the polymeric coupler phase may contain dyes and pigments to provide the required optical density of the final image. Pigments such as carbon black are preferred when a very high optical density is required. The layer may also contain a colorless, transparent mordant for dyes. With such a layer, the imaged layer, after removal of uncross-linked areas, may be treated with a dye solution to increase optical density as the dye is adsorbed by the mordant. Such a system avoids the loss of imaging speed which may be experienced if the dye or pigment is present in the photosensitive layer during exposure to radiation.

If an image of high optical density is required, e.g. in the preparation of litho film, the dye or pigment that provides the density is preferably contained in the polymeric coupler phase which in turn is overcoated with a photosensitive silver halide layer. The silver halide is most conveniently carried in an unhardened gelatin layer. With such an arrangement, essentially all of the light used for the exposure is available to the silver halide and none is lost by absorption by colorant. During development, the oxidized developing agent diffuses into the colored polymeric coupler phase to effect cross-linking.

The light-sensitive silver halide used in producing images by the process of this invention includes silver chloride, silver bromide, silver iodide, silver chlorobromide, silver iodobromide, and silver chloroiodobromide, either singly or in mixtures. Preparation of the halide may be carried out in the conventional manner in gelatin, or the halide may be formed directly in a solution of the polymeric coupler. The halide may be formed in gelatin, the gelatin removed, and the halide redispersed in a solution of the polymeric coupler. Normally at least four equivalents of silver halide per equivalent of coupler groups are employed. In imaging systems in which all of the silver halide present is not developable, more than four equivalents of silver halide per equivalent of coupler groups are required.

The grain size distribution and sensitization of the silver halide may be controlled to make silver halides suitable for all classes of photographic materials, e.g. general continuous tone, X-ray, lithographic, microphotographic, direct positive, etc. Ordinarily the silver halide dispersions will be sensitized chemically with sulfur, gold, rhodium, selenium, etc., compounds. They may be sensitized spectrally as desired with various sensitizing dyes, e.g. cyanine, 1,1'-diethyl-4,4'-cyanine iodide, 1,1'-diethyl-2,2'-carbocyanine iodide, 1'3-diethylthia-4'-carbocyanine iodide and other methine and polymethine cyanine dyes, kryptocyanines, merocyanines, pseudocyanines, etc.

The photosensitive element also contains various conventional photographic additives, e.g., coating aids such as saponin, alkylarylsulfonic acids or sulfoalkylsuccinic acids; plasticizers, e.g., glycerol or 1,5-pentanediol; antistatic agents; agents to prevent the formation of spots; and the like.

The developing agent employed in the instant invention is of the polyfunctional type, i.e. it contains a minimum of two groups capable of selectively reducing a silver halide latent image and, in their oxidized state capable of coupling with the coupler groups of the polymeric coupler.

The only essential requirement of the coupling reaction between the oxidized polyfunctional developer and the polymeric coupler is that it forms a cross-linked polymer image. Although development efficiency and coupling efficiency are important, the color of the image is not always important. Thus, many developers and couplers that would not be considered suitable for a color photography process of the prior art because of color deficiency may be operable in the instant process.

The preferred developing agents for use in accordance with this invention have the general formula:

in which $D^1$ and $D^2$, alike or different, each denote a substituted or unsubstituted monovalent p-aminophenol or p-phenylenediamine radical attached to $A^1$ through a nitrogen or carbon atom of the radical, and $A^1$ represents a single bond or a divalent organic radical selected from the group consisting of alkylene, arylene, oxydialkylene, oxydiarylene, alkylarylene, arylalkylene, and a radical which contains a divalent p-aminophenol or p-phenylenediamine radical; and when $D^1$ and $D^2$ are attached to $A^1$ through a carbon atom, $A^1$ additionally includes sulfide, ether, amino, amide, alkylamino, acyl and carbonyl.

An especially preferred class of developing agents has the general formula

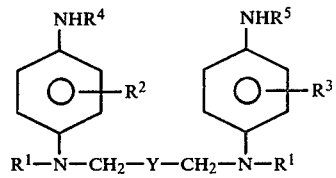

wherein $R^4$ and $R^5$, alike or different, are H or substituted alkyl of 1–6 carbons wherein the substituents are $CO_2H$, $SO_3H$ or $PO_2H_2$ groups, preferably H;

$R^2$ and $R^3$, alike or different, are H, Cl, alkyl, alkoxy, hydroxyalkyl, aminoalkyl, alkylamino, dialkylamino, acetamido, acetamidoalkyl, alkylsulfonamido or alkylsulfonamidoalkyl wherein any alkyl groups are of 1–3 carbons;

$R^1$ is H, alkyl, hydroxyalkyl, or aminoalkyl in which the amino group may be substituted and alkyl is 1–6 carbons; or the two $R^1$ substituents taken together are $-CH_2CH_2-$;

Y is $-(CH_2)_q-$, $-(CH_2)_q-O-(CH_2)_r-$, $-(CH_2)_q-$, $CH(OH)-(CH_2)_r-$, and $-(CH_2)_q-N(CH_3)-(CH_2)_r-$ in which q and r, alike or different, are whole numbers 0–8.

Examples of suitable developing agents include:
N,N'-bis(β-hydroxyethyl)-N,N'-bis[4-amino-3-methyl)-phenyl]tetramethylenediamine,
N,N'-dimethyl-N,N'-bis(4-aminophenyl)trimethylenediamine,
N,N'-bis[(4-amino-3-methyl)phenyl]-N,N'-(dimethyl)ethylenediamine,
β,β'-oxybis[β-(N-ethyl-4-aminoanilino)ethyl]ether,
N,N'-bis(β-hydroxyethyl)-N,N'-bis[(4-amino)phenyl]ethylenediamine,
1,2-bis[(2,5-diamino)phenyl]ethane,
2,2'-bis(dimethylamino)-5,5'-diaminobiphenyl,
N-[2-(N,N-diethylamino)-5-aminophenethyl]-2-amino-5-(N,N-diethylamino)-N-phenylaniline,
2-[β-{2-amino-5-(N,N-diethylamino)phenoxy}-ethyl]-4-amino-N,N-diethylaniline,
bis(2-hydroxy-5-aminobenzyl)amine,
2,2'-methylenebis(4-aminophenol),
N-(2'-hydroxy-5'-aminophenyl)-2-hydroxy-5-aminobenzylamine,
3-methyl-4-amino-N-ethyl-N-(2-hydroxy-5-aminobenzyl)aniline,
2,2'-oxybis(4-amino-6-methylphenol),
5-aminosalicyclic acid(2-amino-5-hydroxy)anilide,
2,2'-disulfidebis(4-aminophenol), and
2,6-bis(2-hydroxy-3-methyl-5-aminobenzyl)-3,5-dimethyl-4-aminophenol.

The developing agents can be prepared directly by conventional means; German Patent Specification No. 2,650,764 and U.S. Pat. No. 3,694,138 list preferred preparative procedures.

The developing agent may be employed in a developer solution. The developer solution contains the developing agent in water or water-soluble organic solvents. However, the developing agent can also be incorporated in the photosensitive element itself, e.g. as a subcoating or integrally mixed with the polymeric coupler, to provide an integral structure containing the developing agent. When the developing agent is incorporated in the photosensitive layer, it is generally advantageous to utilize a protected or masked developer so that premature oxidation and reaction of the developer is prevented. Such developers are well known in the art, e.g. in British Patent No. 541,727. In this latter case, the solution employed in the developing step is an activator solution, e.g. aqueous base.

The developer solutions used according to the invention may contain additives conventionally employed in developer solutions. For example, alkaline agents such as sodium hydroxide, ammonium hydroxide, potassium carbonate, potassium bicarbonate, and sodium carbonate are useful as development accelerators. Conventional developer super additives may be added, e.g. 1-phenyl-3-pyrazolidone (Phenidone) and N-methyl-p-aminophenol (Metol). The super additive may be added directly to the developer solution or it may be incorporated within the photosensitive element. Alternatively, when the developing agent is incorporated in the photosensitive element, the super additive may be added to the activator solution. Sodium sulfate may be used as a swelling suppressant; hydroxylamine salts and sodium sulfite are used as antioxidants; antifoggants include 6-nitrobenzimidazole salts and alkali metal halides such as potassium bromide; solubilizing agents include benzyl alcohol, 2-ethoxyethanol, 2-methoxyethanol, 2-butoxyethanol and 2-(2-butoxyethoxy)-ethanol. Water softeners, wetting agents, and pH buffers and the like may also be present. The pH of the developer solutions is preferably about 9 to about 12.5, and most preferably about 9.4 to about 10.5.

The pH and salt content of the developer solutions are adjusted so that swelling but not dissolution of the photosensitive layer occurs during the developing step. For example, when a water-soluble hydrophilic polymeric coupler is used, the salt concentration of the developer solution is increased to decrease the solubility of the coupler. When a water-insoluble polymeric coupler is used, the pH of the developer solution is increased and the salt concentration is adjusted so that swelling but not dissolution of the polymeric layer occurs.

The quantity of developing agent employed is not critical. When developer solutions are employed, the developing agent should amount to about 0.1 to about 10 g/l of solution, preferably about 0.25 to about 4 g/l. Because of low solubility of the large developer molecules, it is most convenient to employ essentially a saturated solution of the developing agent.

The ratio of developing agent to polyfunctional coupler is not critical, but sufficient developing agent should be present to effect satisfactory coupling and cross-linking. Preferably, at least about 0.5 mole of developing agent for each equivalent of coupler group is employed.

The photosensitive elements described herein may comprise coatings applied to a wide variety of substrates. By "substrate" is meant any natural or synthetic support, preferably one which is capable of existing in a flexible or rigid film or sheet form. For example, the substrate can be glass, a metal sheet or foil, e.g., copper; a sheet or film of synthetic organic resin; cellulose paper; fiberboard; and the like, or a composite of two or more of these materials. Suitable substrates include those described in U.S. Pat. Nos. 2,760,863, 3,060,026, and 3,458,311. Preferred substrates are thin, flexible, and may have a hydrophilic surface, e.g., grained aluminum sheets, steel sheets, polyvinylidene chloride copolymer-coated oriented polyester film, and gelatin-coated oriented polyester film.

The particular substrate will generally be determined by the use application involved. For example, the photosensitive compositions of this invention are particularly useful for the preparation of lithographic plates when an aluminum substrate is used. Aluminum substrates are available commercially in a wide variety of thicknesses. The aluminum may be untreated (except for the thin layer of oxide which forms immediately at its surface when exposed to air), or it may have been provided with surface treatments or coatings to leave a hydrophilic or less reactive surface. The surface can be roughened (mechanically, chemically, or electrochemically) to improve retention of aqueous liquids and to improve adhesion to strata to be applied thereon.

The photosensitive element employed in the invention may consist of one or more layers on a substrate as described heretofore. The element may also contain a top-coat or protective stratum. Such top-coats should be transparent to light and water-permeable, preferably water-soluble. The layer or layers are usually applied to the substrate as a solution or dispersion in a carrier solvent. The solution or dispersion may be sprayed, brushed, applied by a roller or an immersion coater, flowed over the surface, picked up by immersion, spin-coated, or applied to the substrate by other suitable means. The solvent is then allowed to evaporate. In general, solvents are employed which are volatile at ordinary pressures. Examples of suitable solvents include water, aqueous ammonia, and mixtures of water with water-miscible organic solvents such as methanol, ethanol, butanol, 2-methoxyethanol, 2-ethoxyethanol, 2-butoxyethanol, etc. When the photosensitive element contains a separate silver halide layer, the polymeric coupler layer may be applied to the substrate using an organic solvent, e.g., a chlorinated hydrocarbon, ketones, or alcohols, and the silver halide emulsion is subsequently applied from an aqueous solution. It may also be applied from an alcohol dispersion, as described in German Patent Specification No. 2,652,456.

The thickness of the photosensitive element, after drying, is usually about 0.02 to about 3 mils (0.5–75 microns), preferably about 0.05 to about 0.3 mil (1.25–7.5 microns).

Imagewise exposure of the photosensitive layer is conveniently carried out by exposing the layer by any of the procedures used with the usual silver halide photographic materials, e.g., camera, cathode ray tube, light emitting diode, projection, contact or laser processes. In most applications the original copy used for camera exposure will consist of black and white areas only; or, if used for contact or projection printing, it will consist of opaque and clear areas (process transparency). Exposures are normally made directly onto the photosensitive element. However, when high concentrations of colorant are present in the silver halide-containing layer, exposure is preferably made through a transparent substrate to provide proper anchorage of the image to the substrate. When the photosensitive element contains a pigmented polymeric coupler layer and a separate superior silver halide emulsion layer, exposure may be made directly onto the silver halide layer. If an appropriate concentration of light-absorbing dye or pigment is present throughout the thickness of the photosensitive element so that the light is attenuated as it passes through the element, exposures to continuous tone copy can be made through the transparent support. Alternatively, the exposed and developed layer can be transferred to another support before removing the undeveloped, noncross-linked areas. The image obtained is of varying thickness and is continuous tone.

The process of the invention may be employed for the preparation of both negative and positive images. Positive images may be obtained by reversal processing using either light fogging or a chemical fogging agent. Direct positives may be obtained using the prefogging technique.

The undeveloped, noncross-linked areas of the polymeric coupler layer are removed by washing with water, an aqueous solution of solids such as alkali metal carbonates, hydroxides, silicates, phosphates, sulfates, and halides, or a semiaqueous solution of water and a water-miscible organic solvent. Suitable organic solvents include methanol, ethanol, 2-propanol, 2-ethoxyethanol, 2-butoxyethanol, 2-(2-butoxyethoxy)ethanol, and glycerol. Spray washout and brushing are preferred for removal of the undeveloped areas. When a separate silver halide emulsion layer is employed, this entire layer is removed during the washing step.

For certain applications, one or more conventional posttreatment or finishing steps may be included. Such steps include fixing, treatment with an oxidizing agent, acid treatment, hardening with polyvalent metal ions, e.g., calcium, magnesium or borate ions, treatment with a surface active agent, etc. The element is dried in a conventional manner.

The following are illustrative examples of the invention in which all parts, percentages and ratios are by weight and all degrees are Celsius unless otherwise stated.

EXAMPLE 1

A. Preparation of Polymeric Coupler

A slurry of 75 g of low molecular weight (Mn~10,000) partially hydrolyzed polyvinyl alcohol (12–15% residual acetoxy groups) in 200 ml of dioxane, 2.2 ml of 85% phosphoric acid, 2.0 ml of water and 10 g of salicylaldehyde is heated at reflux with stirring for 14 hours. The phosphoric acid is then neutralized with triethylamine, and the solid is separated by filtration. The solid is washed with dioxane, then with acetone and finally dried. By light absorbance measurements at ca. 275 nm on dilute solutions of the polymer in water and 1/1 ethanol/water, it is found that the product contains ca. 2% polyvinyl salicylal groups. The salicylal of trimethylene glycol is used as a reference standard.

B. Preparation of Bifunctional Developing Agent

The bifunctional developing agent, N,N'-bis(β-hydroxyethyl)-N,N'-bis[(4-amino-3-methyl)phenyl]tetramethylenediamine, is prepared by the following sequence of reactions:

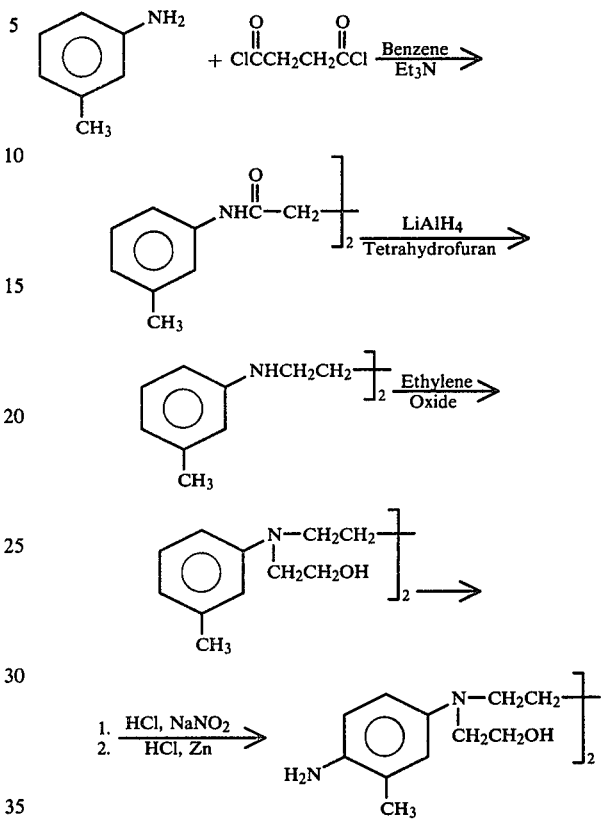

The product is purified by preparation of the tetrahydrochloride salt, mp 162°–165°.

Anal. Calcd for $C_{22}H_{38}N_4O_2Cl_4$: C, 49.63; H, 7.19; N, 10.53; Cl, 26.64. Found: C, 49.41; 49.85, 49.90; H, 7.36, 7.55, 7.65; N, 10.23; Cl, 24.46, 24.70.

Proton nmr spectrum ($D_2O$/3-trimethylsilyl-1-propanesulfonic acid sodium salt (DDS)): Hz 442–463 (6); 205–294 (m, 19); 199 (s, 6); 67–116 (m, 5).

C. Emulsion Preparation and Coating

To 10 ml of a 7% solution of the polyvinyl salicylal of part A in water/ethanol (70/30 by vol) are added simultaneously with stirring 2.5 ml of 0.1 N silver nitrate and 2.5 ml of 0.1 N potassium bromide solutions. The resulting silver bromide suspension in polyvinyl salicylal is flow-coated onto 2"×3" (5.08 cm×7.6 cm) glass plates in normal room lighting and allowed to dry. This procedure furnishes a polymeric coupler coating containing fogged silver bromide.

D. Development

An alkali stock solution, pH=11.2, is prepared by dissolving 12.5 g of sodium carbonate and 0.5 g of sodium sulfite in sufficient water to give 500 ml of solution. The stock solution is then used to prepare working developer solutions as follows:

| Dev. 1 A (bifunctional) | |
|---|---|
| Alkali stock solution | 10 ml |
| N,N'-bis(β-hydroxyethyl)-N,N'-bis-[(4-amino-3-methyl)phenyl]- | |

| | |
|---|---|
| tetramethylenediamine hydrochloride | 50 mg |
| Dev. 1 B -Control (monofunctional) | |
| Alkali stock solution | 10 ml |
| p-aminodiethylaniline hydrochloride | 50 mg |

Individual drops of developers 1 A and 1 B are placed side by side on the light-fogged emulsion coating of part C and allowed to act for 5 minutes. In this time the silver bromide is reduced to metallic silver and the developers are oxidized and coupled with the phenolic coupler groups present in the binder to form a blue dye. The result is similar blue-gray spots on the slightly opalescent undeveloped background.

When the plate is washed in water, the undeveloped areas, as well as the blue-gray spot where control developer 1 B is present, wash away leaving only the blue-gray spot where the bifunctional developer 1 A is present. This shows that the bifunctional developer has cross-linked the originally soluble polyvinyl salicylal binder making it insoluble in water. With the control monofunctional developer 1 B no cross-linking takes place and the binder remains soluble in water.

EXAMPLE 2

A. Preparation of Polymeric Coupler

By the same procedure as described in Example 1, a polyvinyl salicylal is prepared using twice the amount of salicylaldehyde used in Example 1. The product is found to contain ca. 9% polyvinyl salicylal as shown by UV absorbance measurement.

B. Emulsion Preparation and Coating

To 20 g of a 10% solution of the polyvinyl salicylal of part A in ethanol/water (1/1) is added 8.6 ml of 1 N ammonium bromide solution. The mixture is heated to 40° and stirred while there is added 8.0 ml of 1 N silver nitrate solution to which has been added sufficient concentrated ammonia solution (ca. 1.1 ml) to redissolve the brown precipitate first formed. The dispersion is stirred for 30 minutes at 40° and then cooled to room temperature. The silver bromide content is approximately 36% of the total solids in the mixture. The dispersion is flow-coated onto four 2×3 inch (5.08×7.6 cm) glass plates which are weighed after the coating has dried. The silver bromide coating weight is approximately 10 mg/dm$^2$.

C. Development

An alkali stock solution, pH=12.95, is prepared by dissolving 20 g of trisodium phosphate dodecahydrate, 2.8 g of sodium hydroxide, 1.0 g of sodium sulfite, and 2.5 ml of benzyl alcohol in sufficient water to give 500 ml of solution. The stock solution is combined with various developing agents to prepare working developer solutions as follows:

| 2 A (bifunctional) | |
|---|---|
| Alkali stock solution | 10 ml |
| N,N'-bis($\beta$-hydroxyethyl)-N,N'-bis[(4-amino-3-methyl)phenyl]-tetramethylenediamine hydrochloride | 50 mg |
| 2 B - Control (monofunctional) | |
| Alkali stock solution | 10 ml |
| p-aminodiethylaniline hydrochloride | 50 mg |

| 2 C - Control (monofunctional) | |
|---|---|
| Alkali stock solution | 10 ml |
| 4-amino-3-methyl-N-ethyl-N-($\beta$-methylsulfonamidoethyl) aniline sulfate | 50 mg |

Individual drops of developer solutions 2 A, 2 B, and 2 C are placed on the light-fogged emulsion coating of part B at intervals and allowed to act for 1, 2, and 5 minutes and then rinsed off with water at 40°. Although all the areas treated with the developers became blue-gray as the result of the formation of silver and the coupling reaction, only the spots treated with bifunctional developer 2 A remain after rinsing in water.

EXAMPLE 3

The above examples show that a bifunctional developer is capable of reducing fogged silver halide and that the oxidized developer is capable of coupling with the polymeric coupler to cross-link the polymer. In order to show that the bifunctional compound is a true selective developer, i.e., able to distinguish between exposed and unexposed silver halide and capable of coupling with conventional couplers, a set of color film processing solutions of the "C-22" type is prepared according to the formulas given by E. Gehret in British Journal of Photography, Vol. 109, pages 648–649 (1962). The bifunctional developer solution is modified as follows:

| | |
|---|---|
| Benzyl alcohol/diethylene glycol (1/3 vol) | 20 ml |
| Potassium bromide | 1.7 g |
| Sodium metaborate dihydrate | 84 g |
| Sodium sulfite | 1.85 g |
| N,N'-bis($\beta$-hydroxyethyl)-N,N'-bis[(4-amino-3-methyl)phenyl]tetra-methylenediamine hydrochloride | 5.0 g |
| Sequestering agent | 2.5 g |
| Sufficient water to prepare 1000 ml of solution | |

The pH of the solution is adjusted to 10.6 by addition of sodium hydroxide solution.

A strip of unexposed color transparency film is fogged at one end and a length containing both fogged and unexposed areas is developed for 14 minutes at 26° in the modified C-22 type developer solution. The strip is then subjected to the balance of the processing as described by Gehret: stop bath, 4 min; hardener, 4 min; wash, 4 min; bleach, 6 min; wash, 4 min; fix, 8 min; wash, 8 min. A strip of film is obtained which is dense black at the fogged end and amber in the unexposed area. The light-exposed edge markings (frame numbers and film type) on the film are reproduced clearly as black letters on an amber background in the unexposed section of the film.

EXAMPLE 4

A. Preparation of Polymeric Coupler

A polyvinyl salicylal is prepared as described in Example 1 except that the reaction time is increased to 16 hours. The product is found to contain ca. 7% of polyvinyl salicylal groups as shown by UV absorbance measurement.

B. Preparation of Silver Halide Dispersion

Under photographic safelights a curd of AgCl/AgBr (70/30 molar ratio) is prepared by coagulating a gelatin dispersion of the halide mixture with a polymer containing a plurality of sulfonic acid groups. The coagulum is washed with water to remove soluble salts and essentially all of the gelatin and polysulfonic acid, and then redispersed in water by suspending 75 g of the wet curds (40% silver halide) in 225 ml of distilled water, adjusting the pH to 6.5 with 10% sodium bicarbonate solution, and stirring for 30 minutes at 40°. The potential of the dispersion (Ag/AgCl electrode pair) is adjusted to 150 millivolts by addition of 0.1 N potassium bromide solution. The dispersion is then treated with a small amount of gold thiosulfate and sodium thiosulfate and heated at 52° for 20 minutes. After addition of a stabilizer the mixture is cooled to room temperature. The Ag/AgCl electrode E.M.F. is 110 millivolts.

C. Emulsion Preparation and Coating

To 100 g of an 8.7% aqueous solution of the polyvinyl salicylal of Part A is added 40.5 g of the silver halide dispersion of part B and the composition is stirred thoroughly, pH=8. The mixture is filtered through paper and spin-coated onto (1) 2×3 inch (5.08×7.6 cm) glass plates coated with a thin layer of polyvinyl propional as an anchor layer and (2) 2×3 inch (5.08×7.6 cm) pieces of polyvinyl alcohol-subbed polyester film base to give coating weights of 11.7–16.9 mg/dm$^2$ which correspond to silver halide coating weights of 3.8–5.4 mg/dm$^2$.

D. Exposure and Development

An alkali stock solution, pH=11.6, is prepared by dissolving 50 g of sodium carbonate and 2.5 g of sodium sulfite in sufficient water to give 500 ml of solution. A working developer solution is prepared by combining 60 ml of this stock solution with 150 mg of N,N'-bis($\beta$-hydroxyethyl)-N,N'-bis[4-amino-3-methyl)phenyl]tetramethylenediamine hydrochloride. One of the coated glass plates of part C is exposed for ca. 2 sec using an Air Force resolution-test process transparency to a 15-watt tungsten lamp at 30 inches (76 cm). The exposed plate is developed for 2 min in the developer solution and then rinsed in running water for ca. 30 seconds to remove the unexposed coating. A sharp blue image on a clear background is obtained. Microscopic examination of the image shows a resolution of 60–80 line pairs/mm.

A target consisting of white bristol board with black tape and black ink markings together with a section of newspaper page is arranged on a copy board in front of a camera and illuminated by a photo flood lamp. A reflected light exposure meter reading from the white bristol board indicates an exposure of 0.1 second at f 22 is required for an ASA film speed of 100. A strip of the coated film of part C is placed in the camera and given an exposure of 20 seconds at f 22. The film is developed for 2 minutes in the developer solution, washed in running water, and dried. The area of the image representing the white bristol board and the black tape and ink markings is excellent with good contrast showing clear lines on a blue background. The image area corresponding to the newsprint has less contrast because the grayish newsprint reflects less light than the bristol board.

Another strip of film is exposed in a camera to an outdoor scene on a slightly overcast day. The scene includes a building with white walls and dark window areas. The reflected light exposure meter indicates that an exposure of 1/15 sec at f 32 is required for a film with a speed of ASA 100. The actual exposure given is 0.2 sec at f 1.7 corresponding to an ASA film speed of approximately 0.1. After the film strip is developed and washed, a contrasty negative image of the building is obtained.

E. Lithographic Plate Preparation

A silver halide/polyvinyl salicylal emulsion of part C is fogged by exposure to light and then spin-coated onto a grained aluminum plate. After drying, the plate is spotted with Developer Solution C of Example 5 for 3 minutes, then washed in running water to remove undeveloped areas. A pattern of dark blue spots on a bright aluminum background is obtained. The wet plate is rolled with lithographic developing ink which is accepted by the image spots and rejected by the wet aluminum surface. A print is obtained by pressing the inked plate against paper.

EXAMPLE 5

This example illustrates the difference between a bifunctional developer of the invention and a conventional hydroxy-spiro-bis-indane photographic gelatin tanning agent.

Alkali stock solutions are prepared as follows:

Stock Solution A

A mixture of 50 g of sodium carbonate and 0.5 g of sodium sulfite is dissolved in sufficient water to give 400 ml of solution.

Stock Solution B

A mixture of 0.25 g of potassium pyrosulfite and 2.5 g of N,N'-bis($\beta$-hydroxyethyl)-N,N'-bis[(4-amino-3-methyl)phenyl]tetramethylenediamine hydrochloride is dissolved in sufficient water to give 50 ml of solution.

Working developer solutions are prepared as follows:

Developer Solution C (bifunctional)

A solution of 8.0 ml of stock solution A, 1.0 ml of stock solution B and 1.0 ml of water is prepared.

Developer Solution D - Control (tanning agent)

A solution of 10 ml of stock solution A, 50 mg of propyl gallate and 50 mg of 3,3,3',3'-tetramethyl-5,5',6,6'-tetrahydroxy-spiro-bis-indane tanning agent is prepared.

A glass plate coated with the polyvinyl salicylal/silver halide composition as described in Example 4 C is fogged by exposure to light and then spotted with drops of developer solutions C and D. After five minutes the developers are rinsed off and the plate washed in running water. Only the spots treated with developer solution C remain as blue-gray areas. Although darkening of the spot treated with the control developer solution D is observed, the resin is removed during washing indicating that cross-linking has not occurred.

EXAMPLE 6

This example illustrates an element containing developing agent.

A sub composition is prepared by mixing 1.3 parts of polyvinyl propional, 32.1 parts of ethanol, 50.0 parts of n-butanol and 16.6 parts of water. A portion of this mixture is treated with a small amount of N,N'-bis($\beta$-hydroxyethyl)-N,N'-bis[(4-amino-3-methyl)phenyl]tetramethylenediamine hydrochloride and the solution is spin-coated onto a glass plate to give a polyvinyl propional sub-layer containing the developing agent (Plate A). A second portion of the sub composition is spin-coated in the same manner to give a control sub coating (Plate B) containing no developing agent. Plate B has a coating weight of ca. 2.5 mg/dm$^2$.

A silver bromochloride/polyvinyl salicylal emulsion of Example 4 C is fogged by exposure to light, coated onto plates A and B, and the coatings dried. Drops of stock solution A of Example 5 are spotted on the the coated plates A and B at one minute intervals and allowed to remain for 1, 2, 3, and 4 minutes after which they are rinsed off in running water. In plate A, all the developer-treated areas remain as gray, insoluble spots on the plate. No trace of spots is visible on control plate B.

EXAMPLE 7

This example illustrates the use of carbon black pigment in a composition of the invention.

A. Carbon Black Mix

A carbon black/polyvinyl salicylal composition is prepared by mixing for 5 hours in an attritor mill an 18.6% solution of the polyvinyl salicylal of Example 2 A with channel black pearls in ethanol/water containing a small amount of ammonia. The grind is further diluted with ethanol/water and filtered through a sintered glass filter to give a final composition of approximately 3.9 parts of polyvinyl salicylal, 4.2 parts of carbon black, 37.3 parts of ethanol, 0.8 part of ammonia and 53.8 parts of water.

B. Emulsion Preparation and Coating

Under photographic safelights a light-sensitive emulsion is prepared by combining 20 g of the carbon black mix of part A with 10 g of a silver halide dispersion in water, prepared essentially as described in Example 4 B. The mixture is filtered, and then coated by means of a doctor knife onto an oriented polyester film having a subcoating of a vinylidene chloride copolymer. After drying, the optical density of the coated film is found to be in the range of 1.65–3.55.

C. Exposure and Processing

A developer stock solution is prepared by mixing 0.5 g of potassium pyrosulfite and 1.0 g of N,N'-bis($\beta$-hydroxyethyl)-N,N'-bis[(4-amino-3-methyl)phenyl]tetramethylenediamine hydrochloride with sufficient water to give 20 ml of solution. A working developer solution is prepared by combining 0.5 ml of the developer stock solution with 8.0 ml of stock solution A of Example 5 and 1.5 ml of water. A strip of the coated film of part B is exposed for 10 seconds through the film base substrate using an Air Force resolution-test process transparency to a 15-watt tungsten lamp at a distance of 30 inches (76 cm). The exposed film is developed for 1 minute in the working developer solution, then washed in running water with gentle swabbing with a wad of cotton to assist in removal of the carbon black. The image obtained has clean, sharp lines on a clear background. Microscopic examination shows that resolution is approximately 40–50 line pairs/mm even though during exposure the emulsion side of the process transparency was separated from the photosensitive layer by the thickness of the transparent film base substrate. Shorter and longer exposure times (4 sec; 30 sec) give poorer resolution. Optical density of the images ranges from 2 to 4.

EXAMPLE 8

A. Preparation of Polymeric Coupler

An acrylic copolymer containing pyrazolone coupler groups is prepared by heating at reflux for 8 hours a t-butyl alcohol solution of a mixture of 43 parts of ethyl acrylate, 35 parts of methyl methacrylate, 10 parts of methacrylic acid and 12 parts of 1-phenyl-3-methacrylamido-5-pyrazolone in the presence of 0.4 part of azobisisobutyronitrile initiator, added in portions. The solution is poured into water to precipitate the copolymer, and the precipitated copolymer is steamed to remove volatiles. The number average molecular weight measured by gel permeation chromatography was found to be approximately 32,000 using polymethyl methacrylate standards. A polymer solution is prepared by dissolving 10 g of the copolymer in 85 g of water and 5 ml of concentrated ammonia.

The 1-phenyl-3-methacrylamido-5-pyrazolone is prepared as described in British Patent No. 875,248, Procedure 14.

B. Emulsion Preparation and Coating

Under photographic safelights, a light-sensitive silver halide emulsion is prepared by combining two parts of the polymer solution of part A with one part of a silver halide dispersion in water, prepared essentially as described in Example 4B. The mixture is filtered and spin-coated onto tared glass plates, an oriented polyester film having a subcoating of a vinylidene chloride copolymer, and grained aluminum plates, both silicate treated and anodized types. The coating weights, measured on the glass plates, are in the range of 14–16 mg/dm$^2$ corresponding to a silver halide coating weight of ~5 mg/dm$^2$.

C. Exposure and Processing

Section I

Reversal processing to obtain a positive image is demonstrated with the coated polyester film of part B by exposure for 1 and 2 seconds using an Air Force resolution-test process transparency to a 15-watt tungsten lamp at a distance of 30 inches (76 cm). The exposed films are developed for 2 minutes in a standard high contrast black and white developer (D-19) to reduce the silver halide latent image, treated with a 5% acetic acid solution short stop, and finally washed with water. The resulting films are given an overall exposure to light to fog the previously unexposed silver halide. The exposed films are developed for 2 minutes with the working developer solution of Example 7 C followed by a water wash. Positive images of clear, sharp lines on a magenta background are obtained. Microscopic examination shows resolutions of 32 and 57 line pairs/mm, for the films originally exposed for 1 and 2 seconds, respectively.

Section II

A coated anodized aluminum plate of part B is exposed for 8 seconds as described in Section I. The exposed plate is developed for 2 minutes in the working developer solution of Example 7 C, modified by the addition of 15 ml of 0.1 N potassium bromide solution/100 ml of developer solution. The plate is washed with water and dried to give a clear sharp magenta image, resolution=40 line pairs/mm.

white light by means of a densitometer, and the results are summarized in Table I.

Table I

| Silver Halide/ Binder Ratio (Nominal) | Silver Halide (%) | Silver Halide Coating Weight (mg/dm$^2$) | Optical Density Min. Dev. | Optical Density Max. Dev. | Optical Density of Undev. Areas Washed | Optical Density of Undev. Areas Fixed | Remarks |
|---|---|---|---|---|---|---|---|
| 1/1 | 48 | 8.3 | 0.44 | 0.45 | 0.12 | 0.05 | Heavy haze |
| ½ | 31 | 5.0 | 0.40 | 0.45 | 0.04 | 0.02 | Noticeable haze |
| ⅓ | 23 | 5.6 | 0.34 | 0.45 | 0.03 | 0.01 | Very slight haze |
| ¼ | 19 | 4.3 | 0.28 | 0.43 | 0.03 | 0.02 | Very slight haze |
| 1/5 | 16 | 3.9 | 0.21 | 0.32 | 0.02 | 0.01 | Very slight haze |

Section III

Another coated anodized aluminum plate of part B is exposed for 5 seconds and developed as described in Section II except that a 150 line screen dot pattern showing 2, 5, 50, 95 and 98% dots is used as a process transparency. Excellent reproduction of the 2% through the 95% dots is obtained.

Section IV

Several of the coated grained aluminum plates of part B are exposed for 2–8 seconds through a Bureau of Standards chart showing lines of varying width and developed as described in Section II. Excellent clear, sharp images are obtained which show no variation in image quality within the exposure range used. Images on an anodized aluminum base have slightly better edge sharpness than those on a silicate-treated aluminum base. One of the imaged plates is treated with a lithographic asphalt/gum emulsion, then with fountain solution, and finally rolled with lithographic ink. Very good hand prints are obtained by pressing the inked plate against paper.

EXAMPLE 9

A. Variations in Silver Halide/Binder Ratio

An aqueous solution of the polyvinyl salicylal of Example 4 A is combined with varying amounts of a silver halide dispersion (Example 4 B) to give coating compositions with silver halide/polyvinyl salicylal ratios of 1/1, ½, ⅓, ¼, and 1/5. The compositions are spin-coated in ordinary light onto tared, polyvinyl propional-subbed 2×3 inch (5.08×7.6 cm) glass plates, and the coating weights are determined. The plates are spotted with a developer solution prepared by mixing 8 ml of stock solution A of Example 5, 0.5 ml of stock solution B of Example 5, and 1.5 ml of water. The developer solution is allowed to act for 10, 20, 30 sec, and 1, 2, 3, 4, 5 min; the plates are washed in running water and the ease of removing the undeveloped areas noted. Removal is rapid in all cases, but with the higher silver halide/binder ratios a haze of silver halide particles remains on the surface of the plate. This haze is easily removed with very gentle rubbing. Excess silver halide is removed from the ends of the plates with 10% sodium thiosulfate fixing solution. Optical densities of spot areas and fixed and unfixed background are measured with

EXAMPLE 10

A 1% solution of polyvinyl butyral in ethanol/1-butanol (1/1) is mixed with a sufficient amount of a saturated solution of Oil orange dye in toluene to give a deep orange tint to the mixture. The solution is spin-coated onto 2×3 inch (5.08×7.6 cm) glass plates, and the plates are dried to provide a colored sub-layer. A silver halide/polyvinyl salicylal emulsion, prepared by the procedure of Example 4 C, is spin-coated onto the subcoated glass plates in normal room lighting and allowed to dry. Since the dye is not water-soluble, there is no bleeding of color into the emulsion layer.

The fogged and dried silver halide/polyvinyl salicylal-coated plate is then spotted for 2 minutes with drops of developer solution C (Example 5), and the plate is washed in water and dried. There results a series of black spots developed on an orange background. When the plate is subsequently treated rapidly with a limited amount of toluene, (e.g., in the spin-coating apparatus), the orange dye is removed where it is not protected with the cross-linked polyvinyl salicylal in the developed areas. Hence, developed black spots remain on a colorless background.

EXAMPLE 11

This example demonstrates an adjacent layer effect and incorporation of a bifunctional developer into the photosensitive element.

A. Coating of Polymeric Coupler and Bifunctional Developer

The bifunctional developer free base, N,N'-bis(β-hydroxyethyl)-N,N'-bis[(4-amino-3-methyl)phenyl]-tetramethylenediamine, prepared in Example 1, Part B, is dissolved as follows:

0.072 g bifunctional developer free base,
10.0 ml 8:2 vol/vol mixture of methylene chloride and 1,1,2-trichloroethane, and
0.50 ml methanol are mixed.

Then 0.75 g of the acrylic copolymer containing pyrazolone coupler groups prepared in Example 8, Part A, is added and quickly brought into solution by tumbling. The solution is filtered, protected from air by a nitrogen atmosphere, and spin-coated onto 2×2 inch (5.08×5.08 cm) anodized aluminum plates at 3000 rpm to give coating weights of 16.7 mg/dm². The coatings are clear, smooth and colorless.

B. Overcoating with Silver Halide Emulsion

An ortho-sensitized small-grained silver bromide emulsion in which the gelatin/AgBr ratio is 44/56 and the solids/water ratio is 11/89 is spin-coated at 2000 rpm and 52° onto the 2×2 inch (5.08×5.08 cm) plates which are precoated with polymeric coupler and bi-functional developer to give AgBr/gelatin coating weights of 9.7 mg/dm². This corresponds to 3.7 equivalents of silver bromide for every equivalent of pyrazolone coupler group.

C. Exposure and Processing

A plate is held in contact with an Air Force resolution-test process transparency and exposed one second to a 15-watt tungsten lamp at a distance of 30 inches (76 cm). The exposed plate is developed for four minutes with a 20% potassium carbonate solution and treated with a 2% acetic acid/20% potassium chloride short stop. At this point the plate has a dark silver image in the gelatin layer superimposed over a magenta transfer image in the acrylic copolymer layer. Maximum diffuse reflective density is 1.25. The silver/gelatin layer is removed by rubbing the plate in hot water leaving a magenta transfer image with diffuse reflective density 1.84 and resolution exceeding 10 line pairs per millimeter. When the plate is treated with 20% potassium carbonate for two minutes followed by 10% potassium chloride, the unimaged areas are removed before the imaged areas.

EXAMPLE 12

This example illustrates the preparation of large plates and their use in lithographic printing.

A. Emulsion Preparation and Coating

A polymer solution is prepared by dissolving 10.0 g of the acrylic copolymer containing pyrazolone coupler groups prepared in Example 8, Part A, in 70 ml of water and 1.25 ml of concentrated ammonia. A sensitized silver halide dispersion is prepared by the procedure of Example 4B. Under photographic safelights, a light-sensitive silver halide emulsion is prepared by combining 48 parts of the polymer solution and 50.9 parts of the silver halide dispersion. This corresponds to 8.9 equivalents of silver halide for each equivalent of pyrazolone coupler group. The emulsion is spin-coated at 150 rpm under photographic safelights onto a clean silicate-treated anodized aluminum sheet and air-dried to give coating weights of 20–32 mg/dm².

B. Developer

Stock Solution I

A clear stable solution of 0.5 g of N,N'-bis-(β-hydroxyethyl)-N,N'-bis[(4-amino-3-methyl)phenyl]tetramethylenediamine hydrochloride and 9.5 ml of water is prepared.

Stock Solution II

A mixture of 100.0 g of potassium carbonate and 100.0 g of potassium bicarbonate is dissolved in 800 ml of water.

Stock Solution III

A mixture of 0.100 g 1-phenyl-3-pyrazolidone (Phenidone) and 99.9 g stock solution II is freshly mixed under nitrogen each day to give a clear solution.

Stock Solution IV

A mixture of 1.00 g of sodium sulfite and 99 g of stock solution II is freshly mixed every 1–2 days to give a clear solution.

Developer V is prepared by adding and mixing in sequence: 1.00 ml of stock solution I, 5.00 ml of stock solution III, 2.50 ml of stock solution IV, 17.5 ml of stock solution II, and 24 ml of water. The developer initially is a hazy pale green solution that turns pink and is used within eight hours of mixing.

C. Exposure and Processing

A 7.5×23 inch (19×58.5 cm) piece of the emulsion-coated aluminum sheet prepared in part A is held in close contact, emulsion-to-emulsion, with a 150 line lithographic halftone negative transparency and exposed one second through the transparency to a 15-watt tungsten lamp at a distance of 30 inches (76 ml). Under photographic safelights in near darkness the exposed sheet is transferred to a tray, covered with 900 ml of developer V at 26°, and gently rocked for 2 minutes. The sheet is transferred under safelights to another tray, covered with 900 ml of water and rocked for 2 minutes. The sheet is then washed thoroughly in tap water under safelights and stopped in a solution of 18 g of acetic acid in 882 ml of water for 2 minutes and air-dried. The plate is quite clean, free of scum and has a high resolution image that reproduces the halftone very well. Dark insoluble, cross-linked coating remains on the sheet opposite clear areas in the transparency. Coating defects and other blemishes are removed by spot rubbing with a cotton swab soaked in stock solution II.

D. Printing

The plate is mounted on a Miehle offset lithographic printing press, wet with normal fountain solution and process black lithographic ink, and used to print fifty thousand copies of the halftone image onto paper.

EXAMPLE 13

This example illustrates the use of N,N'-dimethyl-N,N'-bis(4-aminophenyl)trimethylenediamine as a bifunctional developing agent.

A. Preparation of Bifunctional Developing Agent

The bifunctional developing agent, N,N'-dimethyl-N,N'-bis(4-aminophenyl)trimethylenediamine, is prepared by the following sequence of reactions:

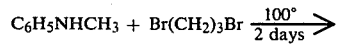

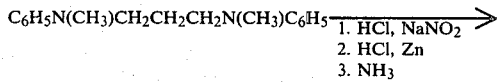

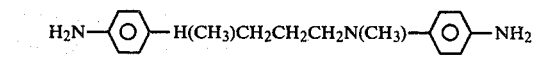

The crude product is purified by high pressure liquid chromatography using a 90/10 methylene chloride/methanol elution solvent to give a fairly pure viscous product which contains two minor impurities. Proton nmr spectrum (CDCl$_3$/tetramethylsilane): δ 6.59 (s, 8); 2.2–4.0 (m, 16) and 1.58 ppm (q, 2), is consistent with the assigned structure.

Anal. Calcd. for C$_{17}$H$_{24}$N$_4$: C, 71.79; H, 8.51; N, 19.70 Found: C, 71.41, 71.55; H, 8.43, 8.64; N, 18.06, 17.82.

B. Emulsion Coating

The emulsion of Example 12 Part A is spin-coated at 300 rpm under photographic safelights onto a clean silicate-treated anodized aluminum sheet, and the coated sheet is air-dried to give a coating weight of 16 mg/dm$^2$.

C. Developer

Solution A

A mixture of 0.28 g of N,N'-dimethyl-N,N'-bis(4-aminophenyl)trimethylenediamine, 2 ml of 2 N hydrochloric acid, and 6.3 ml of water gives a clear solution.

Developer B is prepared by mixing 1.00 ml of Solution A, 44 ml of Stock Solution II of Example 12, and 5 ml of Stock Solution III of Example 12.

D. Exposure and Processing

A 2×2 inch (5.08×5.08 cm) plate is held in contact with an Air Force resolution-test process transparency and exposed 1 second to a 15-watt tungsten lamp at a distance of 30 inches (76 cm). The plate is covered with Developer B and swirled at room temperature for 2 minutes under photographic safelights, rinsed with gently-flowing water, and finally rinsed with a fine spray of water to give a magenta washout image with resolution of 64 line pairs/mm.

Industrial Applicability

The process of the invention is suitable for a wide variety of pattern and image yielding uses in both negative and positive imaging systems. Specific uses include the preparation of lithographic films, lithographic plates, photographic elements, computer output microfilm, engineering reproduction films, camera speed resists for chemical milling and printed circuit boards, gravure printing, thermal transfer printing, proofing systems and other uses as described in U.S. Pat. Nos. 3,345,164; 3,194,661; and 3,241,962.

I claim:

1. A method for producing a cross-linked polymeric image on a substrate which comprises:
   (a) imagewise exposing a photosensitive element to actinic radiation, said element comprising a substrate coated with a photosensitive layer containing dispersed silver halide in operative association with a continuous film-forming phase of hydrophilic polymeric coupler having a number average molecular weight of 5,000 to 100,000 and containing, per polymer chain, an average of at least two coupler groups capable of coupling with an oxidized p-aminodialkylaniline;
   (b) swelling the polymeric coupler, and developing the exposed layer with a developing agent containing at least two functional groups capable of selectively reducing a silver halide latent image and, in their oxidized state, capable of coupling with the coupler groups of the swollen polymeric coupler, whereby the polymeric coupler is insolubilized by cross-linking, thereby forming an image; and
   (c) removing the undeveloped, noncross-linked areas of the polymeric coupler by washing with a solvent in which the noncross-linked areas are soluble.

2. The process of claim 1 for producing a negative image in which the insolubilized polymeric image forms in the area exposed to actinic radiation.

3. The process of claim 1 for producing a positive image in which the insolubilized polymeric image forms in the area not exposed to actinic radiation.

4. The process of claim 1 in which the substrate is aluminum.

5. The process of claim 1 in which the coupler groups of the polymeric coupler are indoxyl groups which also function as the developing agent.

6. The process of claim 1 in which the developing agent is of the formula:

$$D^1\text{-}A^1\text{-}D^2$$

in which D$^1$ and D$^2$, alike or different, are substituted or unsubstituted monovalent p-aminophenol or p-phenylenediamine radicals attached to A$^1$ through a nitrogen or carbon atom of the radical, and A$^1$ is a single bond or a divalent organic radical selected from the group consisting of alkylene, arylene, oxydialkylene, oxydiarylene, alkylarylene, arylalkylene, and a radical which contains a divalent p-aminophenol or p-phenylenediamine radical, and when D$^1$ and D$^2$ are attached to A$^1$ through a carbon atom, A$^1$ additionally includes sulfide, ether, amino, amido, alkylamino, acyl and carbonyl.

7. The process of claim 6 in which the photosensitive element contains at least four equivalents of silver halide per equivalent of coupler groups.

8. The process of claim 7 in which the polymeric coupler has a number average molecular weight of 10,000 to 50,000 and contains 0.1 to 1.0 equivalent of coupler group per 1000 grams of polymer.

9. The process of claim 8 in which the coupler groups are selected from the group consisting of phenols, naphthols, amines, aminophenols, bisphenols, pyrazolones, acylacetarylides, cyanoacetarylides, beta-ketoesters, N-homophthalylamines, coumaranones, indoxyls and thioindoxyls.

10. The process of claim 9 in which the base polymer to which the coupler groups are attached is selected from the group consisting of polyvinyl alcohol; partially hydrolyzed polyvinyl acetate; hydrolyzed copolymers of vinyl acetate and other vinyl monomers; homopolymers of acrylic acid, methacrylic acid, methacrylamide, and 2-hydroxyethyl methacrylate; copolymers of acrylic acid, methacrylic acid, methacrylamide and 2-hydroxyethyl methacrylate with other conventional vinyl monomers; poly(ethylene oxide); polyvinyl pyrrolidone; and copolymers of maleic anhydride.

11. The process of claim 10 in which the developing agent is of the formula

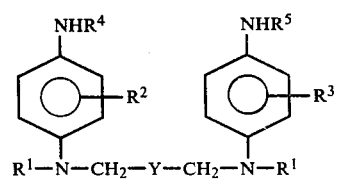

wherein $R^4$ and $R^5$, alike or different, are H or substituted alkyl of 1–6 carbons wherein the substituents are —COOH, —SO$_3$H or —PO$_2$H$_2$ groups;

$R^2$ and $R^3$, alike or different, are H, Cl, alkyl alkoxy, hydroxyalkyl, aminoalkyl, alkylamino, dialkylamino, acetamido, acetamidoalkyl, alkylsulfonamido or alkylsulfonamidoalkyl, wherein any alkyl groups are of 1–3 carbons;

$R^1$ is H, alkyl, hydroxyalkyl, or aminoalkyl in which the amino group may be substituted and alkyl is 1–6 carbons; or the two $R^1$ substituents taken together are —CH$_2$CH$_2$—;

Y is $-(CH_2)_{\overline{q}}$, $-(CH_2)_q O-(CH_2)_{\overline{r}}$, $-(CH_2)_q CH(OH)(CH_2)_{\overline{r}}$ and $-(CH_2)_{\overline{q}} N(CH_3)(CH_2)_{\overline{r}}$ in which q and r, alike or different are whole numbers from 0–8.

12. The process of claim 11 in which the developing agent is employed in the amount of at least 0.5 mole per equivalent of coupler group.

13. The process of claim 12 in which $R^4$ and $R^5$ are hydrogen.

14. The process of claim 13 in which the developing agent is N,N'-bis(β-hydroxyethyl)-N,N'-bis[(4-amino-3-methyl)phenyl]tetramethylenediamine.

15. The process of claim 13 in which the exposed layer is treated with a developing agent in a developer solution.

16. The process of claim 13 in which the developing agent is incorporated in the photosensitive element, and the exposed layer is treated with an activator solution.

17. The process of claim 14 in which the coupler groups of the polymeric coupler are pyrazolone groups.

18. The process of claim 17 in which the substrate is aluminum.

19. The process of claim 1 in which the developing agent is employed in combination with 1-phenyl-3-pyrazolidone.

* * * * *